United States Patent [19]

Shim et al.

[11] 3,962,374
[45] June 8, 1976

[54] METHOD OF PREPARING STABLE CONDENSATION PRODUCTS BY SOLVENT EXTRACTION AND PRODUCTS FORMED BY THE PROCESS

[75] Inventors: Kyung S. Shim, Irvington; Edward N. Walsh, New City, both of N.Y.

[73] Assignee: Stauffer Chemical Company, Westport, Conn.

[22] Filed: Aug. 5, 1974

[21] Appl. No.: 494,427

[52] U.S. Cl. ............................ 260/928; 260/2.5 AJ; 260/2.5 AR; 260/45.7 P; 260/927 R; 260/978; 260/983; 260/989; 260/990
[51] Int. Cl.² ...................... C07F 9/09; C07F 9/40
[58] Field of Search ............... 260/927 R, 928, 982, 260/989, 990, 978

[56] References Cited
UNITED STATES PATENTS

| | | | |
|---|---|---|---|
| 3,641,202 | 2/1972 | Biranowski et al. | 260/928 X |
| 3,822,327 | 7/1974 | Weil | 260/928 |
| 3,855,359 | 12/1974 | Weil | 260/928 |

*Primary Examiner*—Richard L. Raymond
*Attorney, Agent, or Firm*—Richard P. Fennelly

[57] ABSTRACT

Products which are phosphorus containing oligomers having

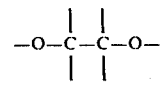

linkages between phosphorus atoms and which are obtained by the self-condensation of β-haloalkyl esters of pentavalent phosphorus acids or by the condensation of these esters with an alkyl ester of a pentavalent phosphorus acid are extracted with an inert organic solvent. The soluble portion of said products after recovery from the solvent can be incorporated in a polyurethane foam formulation to give a foam which will have less scorching than a foam containing the original condensation product that has not been extracted.

13 Claims, No Drawings

METHOD OF PREPARING STABLE CONDENSATION PRODUCTS BY SOLVENT EXTRACTION AND PRODUCTS FORMED BY THE PROCESS

TECHNICAL DESCRIPTION OF THE INVENTION

The present invention is a process for forming an improved condensation product of β-haloalkyl esters of pentavalent phosphorus acids which have flame retardant properties. A number of processes for formation of the class of compounds of interest herein are described in the patent literature and in copending applications including the following:

1. U.S. Pat. No. 3,513,644 to Edward D. Weil which describes the preparation of polycondensed oligomeric phosphates by heating of tris(2-haloalkyl) phosphates.

2. U.S. Pat. Nos. 3,641,202 and 3,695,925 to Edward D. Weil which describe the preparation of oligomeric polycondensed phosphonates from bis(haloalkyl) vinyl phosphonates.

3. U.S. Pat. No. 3,896,187 of Edward D. Weil which describes liquid poly(haloethyl-ethylene-oxy) phosphoric acid esters prepared by condensing tris(2-haloethyl phosphate.

4. U.S. Ser. No. 410,583, filed Nov. 12, 1973, now abandoned, and U.S. Pat. No. 3,855,359 of Edward D. Weil which describe the copolycondensation of certain phosphates and phosphonates having a 2-haloalkyl group on at least one of these reactants.

5. U.S. Pat. No. 3,822,327 of Edward D. Weil which describes homo- and co-polycondensates of bis(2-haloethyl) vinylphosphonates.

6. U.S. Pat. No. 3,891,727 of Edward D. Weil which relates generally to condensation products of haloalkyl esters of pentavalent phosphorus acids.

These patents and disclosures insofar as they relate to the condensation products usable in the practice of the instant invention are incorporated herein by reference. The term "condensation product of a β-haloalkyl ester of a pentavalent phosphorus acid" as used herein includes the condensation products produced either by self-condensation reactions of such esters or by a condensation reaction of such a β-haloalkyl ester with other alkyl esters of pentavalent phosphorus acids. The definition also includes the type of condensation products described in U.S. Pat. No. 3,764,640 to Klose.

The process of this invention is particularly applicable to the homopolymerization product of tris(2-chloroethyl) phosphate, to the copolycondensation product of bis(2-chloroethyl) vinylphosphonate and dimethyl methylphosphonate, to the copoly-condensation product of bis(2-chloroethyl) vinylphosphonate and trimethyl phosphate, to the homopolycondensation product of bis(2-chloroethyl) vinylphosphonate, and to the copolycondensation product of tris(2-chloroethyl)-phosphate and dimethyl methylphosphonate.

Briefly, the polycondensation products are produced by reacting the monomer (both of which, as has already been noted may be the same) to give off a volatile alkyl halide or alkylene dihalide and leave behind a nonvolatile oligomeric condensation product.

The polycondensation reaction can be run without a catalyst, but, to permit lower temperatures and/or shorter reaction times, it is preferably conducted in the presence of a basic catalyst. Suitable quantities of catalyst are from a few parts per million, e.g., about 50 p.p.m., up to about 10% by weight, preferably about 0.01 – 5%, based on the weight of the reaction mixture.

The reaction mixture, with proper amount of catalyst, if desired, and in the desired molar ratio of starting materials, is heated to a temperature within the range of from about 110°C. to about 250°C., preferably about 160°C.–190°C. Further details concerning the condensation reaction may be found in the disclosures previously incorporated herein by reference.

It has been suggested in U.S. Pat. No. 3,896,187 in Canadian Pat. No. 908,186, and in Belgian Pat. No. 789,815, that a stabilized condensation product can be formed by treating the condensed ester with an alkylene oxide neutralizing agent until acidic groups in the product, i.e., the residual acid content, are present to an insignificant degree. Alternatively, it has been suggested in U.S. Pat. No. 3,891,727 of Edward D. Weil that treatment with an alcohol or water and then with an epoxide be utilized. However, there was no suggestion in these prior art patents of using an extraction with at least one inert organic solvent to remove medium molecular weight phosphorus oligomers from the product and the recovery and use of only these extracted polymer species in a polyurethane foam formulation.

The types of inert organic solvents which can be used are well known to persons of ordinary skill in the art. Suitable examples are benzene, the halo- substituted benzenes, e.g. chloro and dichlorobenzene, the mono and di- substituted methyl benzenes, e.g. the xylenes and toluene, the $C_5$–$C_{12}$ hydrocarbon solvents, e.g. n-hexane, cyclohexane and n-heptane, and the halogenated methane solvents, e.g., carbon tetrachloride, or mixtures of any of the foregoing solvents. The amount of solvent used will vary depending upon the number of extractions, the particular solvent, the weight of the sample and the temperature of extraction. It is well within the skill of a person in the art to devise the experimental details for suitable procedures. Generally, the extraction temperature will range from room temperature (about 20°C.) to about 150°C. The amount of solvent used will range from a weight ratio of about 4:1 to about 1:10 and the number of extractions will vary from 1 to about 10. Generally, use of ratios of about 1:1 to about 1:4 in about 2 to 5 extractions will suffice.

The solvent is easily removed from the extract under reduced pressure at somewhat elevated temperatures by procedures well known in the art to yield a residue which comprises as a major component the medium weight, rather than higher weight, oligomers of the crude condensation product. When this extracted product is incorporated in a polyurethane foam formulations, very little scorching is noted.

If desired, trace acidity can be removed by treating the product with an alkylene oxide as taught in U.S. Ser. No. 409,486 of Weil.

EXAMPLE 1

Tris(2-chloroethyl) phosphate is condensed by heating it in the presence of about 0.2% $Na_2CO_3$ at 160°–180°C. to form a crude condensation product. About 2 liters (2944g) of this product was placed in a three neck, three liter flask. One liter of xylene (845g) was added and the mixture was stirred vigorously at room temperature. The xylene was siphoned out and retained. This procedure was repeated three additional times. At the conclusion, all four xylene layers were successively placed in a 5 liter flask and were stirred until separation of solid occurred. The xylene layers were then siphoned off into another flask and were aspirator stripped at 100°C./40 mm. Hg. The acid number of the recovered xylene soluble product was 2.0 (ASTM water-acetone method). The non-soluble layer was stripped of xylene and exhibited an acid number of 2.5 (ASTM water-acetone method).

EXAMPLE 2

The xylene soluble and non-soluble products from Example 1 were both incorporated in a polyurethane foam formulation at 10 parts per hundred based on the weight of polyol. The other ingredients in the foam formulation were:

| Ingredients | Amount (g) |
| --- | --- |
| Thanol F-3002 Polyol | 1700 |
| L-548 Silicone | 17 |
| Water | 68 |
| Niax A-1 Catalyst | 1.7 |
| N-ethyl morpholine | 3.4 |
| $T_{10}$ Stannous Octoate | 8.5 |
| Toluene diisocyanate (80%-2,4 isomer, 20%-2,6 isomer) | 885.7 |

The above foams were cured for 10 minutes at about 150°C. The foam containing the xylene soluble product showed substantially less scorching than the non-soluble product.

What is claimed is:

1. A process for forming a stabilized product which is adapted to be used in a polyurethane foam which comprises extracting a crude condensation product derived from condensing a β-haloalkyl ester of a pentavalent phosphoric acid with itself or with an alkyl ester of pentavalent phosphoric acid with at least one inert organic solvent which will solubilize and thereby remove medium molecular weight phosphorus oligomers contained in said crude product and evaporating said solvent to recover the extracted stabilized product.

2. A process as claimed in claim 1 wherein the inert organic solvent is selected from the group consisting of benzene, halo-substituted benzene, the mono and dimethyl substituted benzenes, the $C_5$–$C_{12}$ hydrocarbon solvents, the halogenated methane solvents, and mixtures thereof.

3. A process as claimed in claim 1 wherein the inert organic solvent is selected from the group consisting of benzene, chlorobenzene, dichlorobenzene, the xylenes, toluene, n-hexane, cyclohexane, n-heptane, carbon tetrachloride, and mixtures thereof.

4. A process as claimed in claim 1 wherein the extraction is carried out at a temperature of about 20°C. to about 150°C.

5. A process as claimed in claim 1 wherein the amount of solvent used ranges between a ratio of about 4:1 to 1:10 solvent to crude condensed ester product.

6. A process as claimed in claim 1 wherein the number of extractions that are performed varies between 1 and about 10.

7. A process as claimed in claim 1 wherein the organic solvent is xylene.

8. A process as claimed in claim 1 wherein the amount of solvent used ranges between a ratio of about 1:1 and 1:4 solvent to crude condensation ester product.

9. A process as claimed in claim 1 wherein about 2–5 extractions are performed.

10. A process as claimed in claim 1 wherein the product is further treated with an alkylene oxide to remove residual acidity.

11. A process as claimed in claim 1 wherein the condensation product which is treated is selected from the group consisting of the homocondensation product of tris(2-chloroethyl) vinylphosphonate, the copolycondensation product of bis(2-chloroethyl) vinylphosphonate and dimethyl methylphosphonate, the copolycondensation product of bis(2-chloroethyl) vinylphosphonate and trimethyl phosphate, the homocondensation product of bis(2-chloroethyl) vinylphosphonate, and the copolycondensation product of tris(2-chloroethyl) phosphate and dimethyl methylphosphonate.

12. The product formed by using the process of claim 1.

13. A stabilized product formed by the process of claim 11.

* * * * *